(12) United States Patent
De Jong et al.

(10) Patent No.: US 9,994,837 B2
(45) Date of Patent: Jun. 12, 2018

(54) ENZYME VARIANTS

(71) Applicant: DSM IP ASSETS B.V., Heerlen (NL)

(72) Inventors: René Marcel De Jong, Echt (NL); Ulrike Maria Müller, Echt (NL); Petrus Jacobus Theodorus Dekker, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days. days.

(21) Appl. No.: 15/110,360

(22) PCT Filed: Jan. 13, 2015

(86) PCT No.: PCT/EP2015/050503
§ 371 (c)(1),
(2) Date: Jul. 7, 2016

(87) PCT Pub. No.: WO2015/107050
PCT Pub. Date: Jul. 23, 2015

(65) Prior Publication Data
US 2016/0333331 A1  Nov. 17, 2016

(30) Foreign Application Priority Data

Jan. 14, 2014  (EP) ..................................... 14151124
May 26, 2014  (EP) ..................................... 14169816

(51) Int. Cl.
*C12N 9/38* (2006.01)
*A23L 29/00* (2016.01)
*A23C 9/152* (2006.01)

(52) U.S. Cl.
CPC .......... *C12N 9/2471* (2013.01); *A23C 9/1526* (2013.01); *A23L 29/06* (2016.08); *C12Y 302/01107* (2013.01); *C12Y 302/01108* (2013.01); *A23V 2002/00* (2013.01)

(58) Field of Classification Search
None
See application file for complete search history.

(56) References Cited

U.S. PATENT DOCUMENTS 9,279,135 B2 * 3/2016 Pereira Rodriguez .. C12P 19/02
2011/0265221 A1 * 10/2011 Abad ................. C12N 15/8247
800/275

OTHER PUBLICATIONS

Kuokkanen et al. (Am. J. of Hum. Gen., vol. 78, 2006, pp. 339-344).*
International Search Report dated Mar. 25, 2015, issued in PCT/EP2015/050503.
XP002725702 Database Uniprot 2012.
XP002725703 Database Uniprot 2014.
Mahoney et al., "Thermostability of yeast lactase (*Kluyveromyces marxianus*) in milk." Journal of Dairy Research, vol. 55, No. 3 (1988) pp. 423-433, XP008169824.
Bansal et al., "Production of β-galactosidase by Kluyvero1nyces marxianus MTCC 1388 using whey and effect of four different methods of enzyme extraction on β-galactosidase activity." Indian J. Microbial. (Sep. 2008) vol. 18, pp. 337-341.
Lertwattanasakul et al., "Utlization of capability of sucrose, raffinose and inulin and its less-sensitiveness to glucose repression in thermotolerant yeast *Kluyveromyces marxianus* DMKU 3.1042." AMB Express, vol. 1, No. 1 (2011) pp. 20-20, XP055122178.
Rodrussamee et al., "Growth and ethanol fermentation ability on hexose and pentose sugars and glucose effect under various conditions in thermotolerant yeast *Kluyveromyces marxianus.*" XP055122883, Appl Microbial Biotchnol (2011) vol. 90, pp. 1573-1586.

* cited by examiner

*Primary Examiner* — Hope Robinson
(74) *Attorney, Agent, or Firm* — McBee Moore Woodward & Vanik IP, LLC; Susan McBee; Chester Moore

(57) ABSTRACT

The invention relates to a variant polypeptide having lactase activity. The invention also relates to a nucleic acid sequence encoding such a variant polypeptide, to a nucleic acid construct comprising said nucleic acid sequence, to a recombinant expression vector comprising said nucleic acid construct and to a recombinant host cell comprising said expression vector. Further, the invention relates to a method for producing a lactase variant via use of such a host cell. Also, the invention relates to a method of producing a lactase polypeptide variant. The invention further relates to a composition comprising a lactase variant, to use of such a lactase variant or to the use of a lactase variant-containing composition in the preparation of a dairy product, to a process for the production of a dairy product and to the resulting dairy product.

25 Claims, No Drawings

SEQUENCE LISTING

<160> NUMBER OF SEQ ID NOS: 2

<210> SEQ ID NO 1
<211> LENGTH: 3103
<212> TYPE: DNA
<213> ORGANISM: Kluyveromyces lactis
<220> FEATURE:
<221> NAME/KEY: source
<222> LOCATION: (1)..(3103)
<223> OTHER INFORMATION: /organism="Kluyveromyces lactis"
    /mol_type="unassigned DNA"

<400> SEQUENCE: 1

```
gaagaccaca tgtcttgcct tattcctgag aatttaagga acccccaaaaa ggttcacgaa      60
aatagattgc ctactagggc ttactactat gatcaggata ttttcgaatc tctcaatggg     120
ccttgggctt ttgcgttgtt tgatgcacct cttgacgctc cggatgctaa gaatttagac     180
tgggaaacgg caaagaaatg gagcaccatt tctgtgccat cccattggga acttcaggaa     240
gattggaagt acgtaaacc aatttacacg aacgtacagt accctatccc aatcgacatc      300
ccaaatcctc ccactgtaaa tcctactggt gtttatgcta gaacttttga attagattcg     360
aaatcgattg agtcgttcga gcacagattg agatttgagg gtgtggacaa ttgttacgag     420
ctttatgtta atggtcaata tgtgggtttc aataagggt cccgtaacgg ggctgaattt      480
gatatccaaa agtacgtttc tgagggcgaaa aacttagtgg tcgtcaaggt tttcaagtgg    540
tccgattcca cttatatcga ggaccaagat caatggtggc tctctggtat ttacagagac    600
gtttctttac taaaattgcc taagaaggcc catattgaag atgttagggt cactacaact    660
tttgtggact ctcagtatca ggatgcagag ctttctgtga agttgatgt ccagggttct     720
tcttatgatc acatcaattt cacactttac gaacctgaag atggatctaa agtttacgat    780
gcaagctctt tgttgaacga ggagaatggg aacacgactt tttcaactaa agaatttatt    840
tccttctcca ccaaaaagaa cgaagaaaca gctttcaaga tcaacgtcaa ggccccagaa    900
cattggaccg cagaaaatcc tactttgtac aagtaccagt tggatttaat tggatctgat    960
ggcagtgtga ttcaatctat taagcaccat gttggtttca gacaagtgga gttgaaggac   1020
ggtaacatta ctgttaatgg caaagacatt ctctttagag gtgtcaacag acatgatcac   1080
catccaaggt tcggtagagc tgtgccatta gatttttgtg ttagggactt gattctaatg   1140
aagaagtta acatcaatgc tgttcgtaac tcgcattatc caaaccatcc taaggtgtat   1200
gacctcttcg ataagctggg cttctgggtc attgacgagg cagatcttga aactcatggt   1260
gttcaagagc catttaatcg tcatacgaac ttggaggctg aatatccaga tactaaaaat   1320
aaactctacg atgttaatgc ccattactta tcagataatc cagagtacga ggtcgcgtac   1380
ttagacagag cttcccaact tgtcctaaga gatgtcaatc atccttcgat tattatctgg   1440
tccttgggta acgaagcttg ttatggcaga aaccacaaag ccatgtacaa gttaattaaa   1500
caattggatc ctaccagact tgtgcattat gagggtgact tgaacgcttt gagtgcagat   1560
atctttagtt tcatgtaccc aacatttgaa attatggaaa ggtggaggaa gaaccacact   1620
gatgaaaatg gtaagtttga aaagcctttg atcttgtgtg agtacggcca tgcaatgggt   1680
aacggtcctg gctctttgaa agaatatcaa gagttgttct acaaggagaa gttttaccaa   1740
ggtggcttta tctgggaatg ggcaaatcac ggtattgaat cgaagatgt tagtactgca   1800
gatggtaagt tgcataaagc ttatgcttat ggtggtgact taaggaaga ggttcatgac   1860
ggagtgttca tcatggatgg tttgtgtaac agtgagcata tcctactcc gggccttgta   1920
gagtataaga aggttattga acccgttcat attaaaattg cgcacggatc tgtaacaatc   1980
acaaataagc acgacttcat tacgacagac cacttattgt ttatcgacaa ggacacggga   2040
aagacaatcg acgttccatc tttaaagcca gaagaatctg ttactattcc ttctgataca   2100
acttatgttg ttgccgtgtt gaaagatgat gctggtgttc taaaggcagg tcatgaaatt   2160
gcctggggcc aagctgaact tccattgaag gtacccgatt ttgttacaga gacagcagaa   2220
aaagctgcga agatcaacga cggtaaacgt tatgtctcag ttgaatccag tggattgcat   2280
```

```
tttatcttgg acaaattgtt gggtaaaatt gaaagcctaa aggtcaaggg taaggaaatt    2340
tccagcaagt ttgagggttc ttcaatcact ttctggagac ctccaacgaa taatgatgaa    2400
cctagggact ttaagaactg gaagaagtac aatattgatt taatgaagca aaacatccat    2460
ggagtgagtg tcgaaaaagg ttctaatggt tctctagctg tagtcacggt taactctcgt    2520
atatccccag ttgtatttta ctatgggttt gagactgttc agaagtacac gatctttgct    2580
aacaaaataa acttgaacac ttctatgaag cttactggcg aatatcagcc tcctgatttc    2640
ccaagagttg ggtacgaatt ctggctagga gatagttatg aatcatttga atggttaggt    2700
cgcgggcccg gcgaatcata tccggataag aaggaatctc aaagattcgg tctttacgat    2760
tccaaagatg tagaggaatt cgtatatgac tatcctcaag aaaatggaaa tcatacagat    2820
acccactttt tgaacatcaa atttgaaggt gcaggaaaac tatcgatctt ccaaaaggag    2880
aagccattta acttcaagat ttcagacgaa tacggggttg atgaagctgc ccacgcttgt    2940
gacgttaaaa gatacggcag acactatcta aggttggacc atgcaatcca tggtgttggt    3000
agcgaagcat gcggacctgc tgttctggac cagtacagat tgaaagctca agatttcaac    3060
tttgagtttg atctcgcttt tgaataaagg aagcttagtc ttc                      3103
```

<210> SEQ ID NO 2
<211> LENGTH: 1025
<212> TYPE: PRT
<213> ORGANISM: Kluyveromyces lactis

<400> SEQUENCE: 2

```
Met Ser Cys Leu Ile Pro Glu Asn Leu Arg Asn Pro Lys Lys Val His
1               5                   10                  15

Glu Asn Arg Leu Pro Thr Arg Ala Tyr Tyr Tyr Asp Gln Asp Ile Phe
            20                  25                  30

Glu Ser Leu Asn Gly Pro Trp Ala Phe Ala Leu Phe Asp Ala Pro Leu
        35                  40                  45

Asp Ala Pro Asp Ala Lys Asn Leu Asp Trp Glu Thr Ala Lys Lys Trp
    50                  55                  60

Ser Thr Ile Ser Val Pro Ser His Trp Glu Leu Gln Glu Asp Trp Lys
65                  70                  75                  80

Tyr Gly Lys Pro Ile Tyr Thr Asn Val Gln Tyr Pro Ile Pro Ile Asp
                85                  90                  95

Ile Pro Asn Pro Pro Thr Val Asn Pro Thr Gly Val Tyr Ala Arg Thr
            100                 105                 110

Phe Glu Leu Asp Ser Lys Ser Ile Glu Ser Phe Glu His Arg Leu Arg
        115                 120                 125

Phe Glu Gly Val Asp Asn Cys Tyr Glu Leu Tyr Val Asn Gly Gln Tyr
    130                 135                 140

Val Gly Phe Asn Lys Gly Ser Arg Asn Gly Ala Glu Phe Asp Ile Gln
145                 150                 155                 160

Lys Tyr Val Ser Glu Gly Glu Asn Leu Val Val Lys Val Phe Lys
                165                 170                 175

Trp Ser Asp Ser Thr Tyr Ile Glu Asp Gln Asp Gln Trp Trp Leu Ser
            180                 185                 190

Gly Ile Tyr Arg Asp Val Ser Leu Leu Lys Leu Pro Lys Lys Ala His
        195                 200                 205

Ile Glu Asp Val Arg Val Thr Thr Thr Phe Val Asp Ser Gln Tyr Gln
    210                 215                 220

Asp Ala Glu Leu Ser Val Lys Val Asp Val Gln Gly Ser Ser Tyr Asp
```

```
            225                 230                 235                 240
His Ile Asn Phe Thr Leu Tyr Glu Pro Glu Asp Gly Ser Lys Val Tyr
                    245                 250                 255

Asp Ala Ser Ser Leu Leu Asn Glu Glu Asn Gly Asn Thr Thr Phe Ser
                    260                 265                 270

Thr Lys Glu Phe Ile Ser Phe Ser Thr Lys Lys Asn Glu Glu Thr Ala
                    275                 280                 285

Phe Lys Ile Asn Val Lys Ala Pro Glu His Trp Thr Ala Glu Asn Pro
            290                 295                 300

Thr Leu Tyr Lys Tyr Gln Leu Asp Leu Ile Gly Ser Asp Gly Ser Val
305                 310                 315                 320

Ile Gln Ser Ile Lys His His Val Gly Phe Arg Gln Val Glu Leu Lys
                    325                 330                 335

Asp Gly Asn Ile Thr Val Asn Gly Lys Asp Ile Leu Phe Arg Gly Val
                    340                 345                 350

Asn Arg His Asp His His Pro Arg Phe Gly Arg Ala Val Pro Leu Asp
                    355                 360                 365

Phe Val Val Arg Asp Leu Ile Leu Met Lys Lys Phe Asn Ile Asn Ala
            370                 375                 380

Val Arg Asn Ser His Tyr Pro Asn His Pro Lys Val Tyr Asp Leu Phe
385                 390                 395                 400

Asp Lys Leu Gly Phe Trp Val Ile Asp Glu Ala Asp Leu Glu Thr His
                    405                 410                 415

Gly Val Gln Glu Pro Phe Asn Arg His Thr Asn Leu Glu Ala Glu Tyr
                    420                 425                 430

Pro Asp Thr Lys Asn Lys Leu Tyr Asp Val Asn Ala His Tyr Leu Ser
            435                 440                 445

Asp Asn Pro Glu Tyr Glu Val Ala Tyr Leu Asp Arg Ala Ser Gln Leu
                    450                 455                 460

Val Leu Arg Asp Val Asn His Pro Ser Ile Ile Trp Ser Leu Gly
465                 470                 475                 480

Asn Glu Ala Cys Tyr Gly Arg Asn His Lys Ala Met Tyr Lys Leu Ile
                    485                 490                 495

Lys Gln Leu Asp Pro Thr Arg Leu Val His Tyr Glu Gly Asp Leu Asn
                    500                 505                 510

Ala Leu Ser Ala Asp Ile Phe Ser Phe Met Tyr Pro Thr Phe Glu Ile
            515                 520                 525

Met Glu Arg Trp Arg Lys Asn His Thr Asp Glu Asn Gly Lys Phe Glu
            530                 535                 540

Lys Pro Leu Ile Leu Cys Glu Tyr Gly His Ala Met Gly Asn Gly Pro
545                 550                 555                 560

Gly Ser Leu Lys Glu Tyr Gln Glu Leu Phe Tyr Lys Glu Lys Phe Tyr
                    565                 570                 575

Gln Gly Gly Phe Ile Trp Glu Trp Ala Asn His Gly Ile Glu Phe Glu
                    580                 585                 590

Asp Val Ser Thr Ala Asp Gly Lys Leu His Lys Ala Tyr Ala Tyr Gly
                    595                 600                 605

Gly Asp Phe Lys Glu Glu Val His Asp Gly Val Phe Ile Met Asp Gly
            610                 615                 620

Leu Cys Asn Ser Glu His Asn Pro Thr Pro Gly Leu Val Glu Tyr Lys
625                 630                 635                 640
```

```
Lys Val Ile Glu Pro Val His Ile Lys Ile Ala His Gly Ser Val Thr
                645                 650                 655

Ile Thr Asn Lys His Asp Phe Ile Thr Thr Asp His Leu Leu Phe Ile
                660                 665                 670

Asp Lys Asp Thr Gly Lys Thr Ile Asp Val Pro Ser Leu Lys Pro Glu
                675                 680                 685

Glu Ser Val Thr Ile Pro Ser Asp Thr Thr Tyr Val Ala Val Leu
                690                 695                 700

Lys Asp Asp Ala Gly Val Leu Lys Ala Gly His Glu Ile Ala Trp Gly
705                 710                 715                 720

Gln Ala Glu Leu Pro Leu Lys Val Pro Asp Phe Val Thr Glu Thr Ala
                725                 730                 735

Glu Lys Ala Ala Lys Ile Asn Asp Gly Lys Arg Tyr Val Ser Val Glu
                740                 745                 750

Ser Ser Gly Leu His Phe Ile Leu Asp Lys Leu Leu Gly Lys Ile Glu
                755                 760                 765

Ser Leu Lys Val Lys Gly Lys Glu Ile Ser Ser Lys Phe Glu Gly Ser
770                 775                 780

Ser Ile Thr Phe Trp Arg Pro Pro Thr Asn Asn Asp Glu Pro Arg Asp
785                 790                 795                 800

Phe Lys Asn Trp Lys Lys Tyr Asn Ile Asp Leu Met Lys Gln Asn Ile
                805                 810                 815

His Gly Val Ser Val Glu Lys Gly Ser Asn Gly Ser Leu Ala Val Val
                820                 825                 830

Thr Val Asn Ser Arg Ile Ser Pro Val Val Phe Tyr Tyr Gly Phe Glu
                835                 840                 845

Thr Val Gln Lys Tyr Thr Ile Phe Ala Asn Lys Ile Asn Leu Asn Thr
                850                 855                 860

Ser Met Lys Leu Thr Gly Glu Tyr Gln Pro Pro Asp Phe Pro Arg Val
865                 870                 875                 880

Gly Tyr Glu Phe Trp Leu Gly Asp Ser Tyr Glu Ser Phe Glu Trp Leu
                885                 890                 895

Gly Arg Gly Pro Gly Glu Ser Tyr Pro Asp Lys Lys Glu Ser Gln Arg
                900                 905                 910

Phe Gly Leu Tyr Asp Ser Lys Asp Val Glu Phe Val Tyr Asp Tyr
                915                 920                 925

Pro Gln Glu Asn Gly Asn His Thr Asp Thr His Phe Leu Asn Ile Lys
                930                 935                 940

Phe Glu Gly Ala Gly Lys Leu Ser Ile Phe Gln Lys Gly Lys Pro Phe
945                 950                 955                 960

Asn Phe Lys Ile Ser Asp Glu Tyr Gly Val Asp Glu Ala Ala His Ala
                965                 970                 975

Cys Asp Val Lys Arg Tyr Gly Arg His Tyr Leu Arg Leu Asp His Ala
                980                 985                 990

Ile His Gly Val Gly Ser Glu Ala Cys Gly Pro Ala Val Leu Asp Gln
                995                 1000                1005

Tyr Arg Leu Lys Ala Gln Asp Phe Asn Phe Glu Phe Asp Leu Ala
        1010                1015                1020

Phe Glu
    1025
```

ENZYME VARIANTS

CROSS REFERENCE TO RELATED APPLICATIONS

This application is a § 371 National Stage Application of PCT/EP2015/050503, filed 13 Jan. 2015, which claims priority to EP14151124.6, filed 14 Jan. 2014, and EP14169816.7, filed 26 May 2014.

FIELD OF THE INVENTION

The invention relates to a variant polypeptide having lactase activity. The invention also relates to a nucleic acid sequence encoding such a variant polypeptide, to a nucleic acid construct comprising said nucleic acid sequence, to a recombinant expression vector comprising said nucleic acid construct and to a recombinant host cell comprising said expression vector. Further, the invention relates to a method for producing a lactase variant via use of such a host cell. Also, the invention relates to a method of producing a lactase polypeptide variant. The invention further relates to a composition comprising a lactase variant, to use of such a lactase variant or to the use of a lactase variant-containing composition in the preparation of a dairy product, to a process for the production of a dairy product and to the resulting dairy product.

BACKGROUND OF THE INVENTION

This invention relates to lactase. Lactase or beta-galactosidase (E.C: 3.2.1.23) is an enzyme, which catalyzes the hydrolysis of lactose (a disaccharide) into its component monosaccharides glucose and galactose. Lactose is present in dairy products and more specifically in milk, skimmed milk, cream, ice cream, fermented milk products such as yogurt, many young cheeses and other dairy products. The breakdown of lactose occurs in the intestinal wall of juvenile mammals (among which are humans) by the natural presence of lactase. Only a small part of the adult population has not lost this property and can still digest lactose. The nutritional and functional problems caused by lactose in most adults are caused by a lack of lactase and are well known and described. Members of such populations cannot hydrolyze lactose, which in such cases passes into the large intestine where it results in dehydration, poor calcium absorption, flatulence, belching and cramps, and, in severe cases, even watery explosive diarrhea.

An important industrial application of lactase is in the production of lactose-hydrolyzed milk products for lactose intolerant individuals. Such hydrolyzed milk products include pasteurized milk, UHT-milk and milk reconstituted from all or part of its original constituents with or without intermediate processing steps such as protein hydrolysis. Treatment with lactase may be done prior to or after the heat-treatment of the milk. The lactase treatment may be done by adding the enzyme to the milk or to one of its lactose-containing constituents.

The solubility properties of lactose are such that it may lead to its crystallization when present at high concentration, leading to a sandy or gritty texture in dairy products such as condensed milk, evaporated milk, dry milk, frozen milk, ice cream, and in confectionary products with a high content of milk. Full or partial hydrolysis of lactose by lactase eliminates this problem, providing products with a homogeneous texture and as a result a higher consumer acceptance.

Another industrial application of lactase is to increase sweet taste in lactose containing products like milk or yoghurt. The hydrolysis of lactose in such products results in increased sweet taste as a result of the production of glucose, while the caloric value of the product does not increase. Conversely, the use of lactase may also decrease sugar addition in sweetened dairy products, without compromising the sweet taste.

Another industrial application of lactase is the hydrolysis of lactose products containing dairy components such as bread. Lactose is added in such products to enhance flavour, retain moisture, provide browning and improve toasting properties. Hydrolyzed lactose syrups are promising in terms of e.g. enhancing crust-colour development, improving flavour and aroma, modifying texture, extending shelf life and strengthening loaf structure.

Lactose hydrolysis by lactase in fermented milk products such as yoghurt will increase sweet taste. Also, when the lactase is added prior to the beginning of the fermentative process, it may increase the rate of acid development and thus reduce processing times. The lactase treatment of milk or milk-derived products such as whey makes such products suitable for application in animal feed and pet food for lactose intolerant animals such as cats. The lactose hydrolysis allows the manufacture of higher concentrated whey and at the same time prevents gut problems, similar to those described earlier for lactose-deficient patients. Lactose hydrolyzed whey is concentrated to produce a syrup containing 70-75% solids and is used as a food ingredient in ice cream, bakery and confectionary products.

Lactases have been described and isolated from a large variety or organisms, including micro-organisms. Lactase is often an intracellular component of micro-organisms like *Kluyveromyces* and *Bacillus*. *Kluyveromyces* and especially *K. fragilis* and *K. lactis*, and other yeasts such as those of the genera *Candida, Torula* and *Torulopsis* are a common source of yeast lactases, whereas *B. coagulans, B. circulans* or lactic acid bacteria are well known sources of bacterial lactases. Several commercial lactase preparations, derived from these organisms are available such as MAXILACT® (from *K. lactis*, produced by DSM, Delft, the Netherlands). These lactases are so called neutral lactases since they have a pH optimum between pH=6 and pH=8.

Although yeast neutral lactases are often used in industry to produce lactose-free or lactose-reduced dairy products, the cost-in-use for the enzyme treatment is often high. Main reasons for the relative high cost-in-use of the enzyme are:

In order to maintain hygienic conditions in the production plant the incubation is performed at low temperature. At this temperature the industrially used lactases are not very active and should be added at relative high dosage.

The currently used lactases are inhibited by its products, especially galactose, at later stages of the incubation with lactase. When products with a low residual lactose concentration are required, extra enzyme has to be added to compensate for reduction in activity due to galactose accumulation.

The currently used lactase has a relative low specific activity in milk which requires the use of a high enzyme dosage in application.

Consequently, enzyme dosage and costs for producing lactose-reduced and lactose-free products are relative high.

It is evident that there is a need for one or multiple lactase variant(s) capable of overcoming at least one of the above-mentioned disadvantages.

SUMMARY OF THE INVENTION

The invention relates to a variant polypeptide having lactase activity, i.e. to a lactase variant. A lactase variant of the invention may have one or more improved properties in comparison with a reference polypeptide, the reference polypeptide typically having lactase activity. A reference polypeptide may be a wild-type lactase, for example the lactase from *K. lactis*. Variant polypeptides of the invention may be referred to as "lactase variant", an "improved lactase" and the like. Variants of *Kluyveromyces* neutral lactase were generated that have properties that lead to a reduction of the cost-in-use of such lactases in the production of lactose-reduced or lactose-free dairy products. A lactase variant with an improved property relevant for dairy production may demonstrate:

- a higher specific activity on ONPG;
- a higher specific activity on lactose;
- a higher activity on lactose in milk at low temperature;
- a reduction in galactose inhibition; and/or
- a higher GOS production in milk.

Each of these improvements may be determined as compared with a reference polypeptide. Moreover, a variant polypeptide of the invention may have at least 2 or 3 or 4 improved properties in comparison with a reference polypeptide. Table 1 provides examples of combinations of improved properties.

According to the invention, there is thus provided a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids 233, 257, 258, 263, 274, 284, 297, 415, 440, 483, 619, 621, 622, 633, 862 or 1004 said positions being defined with reference to SEQ ID NO: 2 and wherein the variant has one or more altered properties as compared with a reference polypeptide having lactase activity and wherein said variant has at least 60% sequence identity with SEQ ID NO:2.

The invention also provides:

a nucleic acid sequence encoding a variant of the invention;

a nucleic acid construct comprising such a nucleic acid sequence operably linked to one or more control sequences capable of directing the expression of a lactase in a suitable expression host;

a recombinant expression vector comprising such a nucleic acid construct; and a recombinant host cell comprising such an expression vector.

The invention also relates to a method for producing a lactase comprising cultivating the host cell of the invention under conditions conducive to production of the lactase and recovering the lactase.

Also, the invention relates to a method of producing a lactase polypeptide variant, which method comprises:

a) selecting a polypeptide having lactase activity;
b) substituting at least one amino acid residue corresponding to any of amino acids 233, 257, 258, 263, 274, 284, 297, 415, 440, 483, 619, 621, 622, 633, 862 or 1004 said positions being defined with reference to SEQ ID NO: 2;

c) optionally substituting one or more further amino acids as defined in b);
d) preparing the variant resulting from steps a)-c);

e) determining a property of the variant; and
f) selecting a variant having an altered property in comparison to the lactase comprising the sequence set out in SEQ ID NO: 2 and selecting a variant having at least 60% sequence identity with SEQ ID NO:2, thereby to produce a lactase polypeptide variant.

Further the invention relates to:

a composition comprising the variant of the invention or obtainable by a method of the invention;

use of a variant lactase according to the invention or of a composition of the invention in the preparation of a dairy product;

a process for the production of a dairy product, which method comprises comprising adding an effective amount of a variant lactase according to the invention or of a composition of the invention to milk and carrying out appropriate further dairy product manufacturing steps; and a dairy product obtainable by such process or use.

BRIEF DESCRIPTION OF THE SEQUENCE LISTING

SEQ ID NO 1 sets out the nucleic acid sequence of the wild type lactase gene sequence from *K. lactis*

SEQ ID NO: 2 sets out the amino acid sequence of the lactase sequence from *K. lactis*.

DETAILED DESCRIPTION OF THE INVENTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

Herein, "lactase" or beta-galactosidase (E.C. 3.2.1.23) is an enzyme, which catalyzes the hydrolysis of lactose (a disaccharide) into its component monosaccharides glucose and galactose. Galacto-oligosaccharides (GOS) may be formed during this reaction due to the transferase activity of the lactase enzyme.

Lactase is found in the intestine of young mammals, in plants, fungi, yeasts and bacteria.

The lactase may be a neutral or an acidic lactase. In a preferred embodiment, the variant polypeptide of the invention has neutral lactase activity, i.e. it has its pH optimum between pH=6 and pH=8.

The lactase may be an intracellular or an extracellular produced lactase. In a preferred embodiment, the lactase is intracellular produced lactase.

A gene or cDNA coding for lactase, for example a variant of the invention, may be cloned and over-expressed in a host organism. Well known host organisms that may be used for lactase over-expression include *Aspergillus, Kluyveromyces, Trichoderma, Escherichia coli, Pichia, Saccharomyces, Yarrowia, Neurospora, Lactococcus* or *Bacillus*.

Herein, positions which may be substituted to achieve a variant of the invention are defined with reference to SEQ ID NO: 2 which is the *K. lactis* lactase.

The invention concerns a variant polypeptide having lactase activity as compared with a reference polypeptide having lactase activity. The reference polypeptide may typically be a wild-type polypeptide having lactase activity, such as the lactase of SEQ ID NO: 2 or a related sequence. The reference polypeptide may also be referred to as a parent polypeptide or comparison polypeptide.

More concretely, the invention relates to a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids activity (such as the polypeptide of SEQ ID NO: 2) and wherein said variant has at least 60% sequence identity with SEQ ID NO:2.

A variant polypeptide will typically have at least one improved property as compared to a reference polypeptide, in particular with respect to a property relevant to the use of the variant polypeptide in a process for preparing a dairy product.

In particular, the improved property may relate to activity or specific activity or to a reduction in galactose inhibition or to a higher GOS production in milk.

Table 1 sets out positions that influence specific properties of the variant lactases of the inventions.

TABLE 1

Preferred substitutions defined in relation to SEQ ID NO:2. Different properties like specific activity on ONPG or lactose as substrate, activity in milk at low temperature, reduction of inhibition of the lactase activity by galactose, and a higher galacto-oligosaccharide production in milk, is indicated

|  | preferred variant | most preferred | spec. act. ONPG | spec. act. Lactose | act. Milk | reduction gal inh | high GOS prod |
|---|---|---|---|---|---|---|---|
| T633 | all AA | G | x |  | x |  |  |
| Y440 | all AA | F |  | x | x |  |  |
| A483 | all AA | S | x | x |  |  |  |
| A1004 | all AA | P |  |  | x |  |  |
| A258 | all AA | T |  |  | x |  |  |
| D233 | all AA | V |  |  | x |  |  |
| N263 | all AA | S |  |  | x |  |  |
| K274 | all AA | E |  |  | x |  |  |
| N284 | all AA | S |  |  | x |  |  |
| D257 | all AA | G |  |  | x |  |  |
| E297 | all AA | G |  |  | x |  |  |
| L862 | all AA | V |  |  | x |  |  |
| V619 | all AA | I |  |  | x | x | x |
| T415 | all AA | C, A | x | x |  |  |  |
| M622 | all AA | L | x |  |  | x | x |
| I621 | all AA | V | x |  |  | x |  |

233, 257, 258, 263, 274, 284, 297, 415, 440, 483, 619, 621, 622, 633, 862 or 1004
said positions being defined with reference to SEQ ID NO: 2 and wherein the variant has one or more altered properties as compared with a reference polypeptide having lactase activity and wherein said variant has at least 60% sequence identity with SEQ ID NO:2.

A wild type reference polypeptide may be obtained from any suitable organism. Typically, a wild type reference polypeptide may be obtained from a microorganism, preferably one in which lactase is produced naturally.

Such microorganism includes yeast such as *Kluyveromyces*. A reference polypeptide may be a *K. lactis* wild type sequence.

Preferably, the reference polypeptide is the lactase set out in SEQ ID NO: 2.

A variant polypeptide as described herein is typically a non-naturally occurring polypeptide.

According to the invention, there is thus provided a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids 233, 257, 258, 263, 274, 284, 297, 415, 440, 483, 619, 621, 622, 633, 862 or 1004
said positions being defined with reference to SEQ ID NO: 2 and wherein the variant has one or more altered properties as compared with a reference polypeptide having lactase A variant polypeptide of the invention may demonstrate higher specific activity on ONPG.

The invention thus provides a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids 233, 257, 258, 263, 274, 284, 297, 415, 440, 483, 619, 621, 622, 633, 862 or 1004
said positions being defined with reference to SEQ ID NO: 2 and wherein the variant has higher specific activity on ONPG as compared with a reference polypeptide having lactase activity (such as the polypeptide of SEQ ID NO: 2) and wherein said variant has at least 60% sequence identity with SEQ ID NO:2.

Preferably, the invention provides a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids 415, 483, 619, 621, 622 or 633
said positions being defined with reference to SEQ ID NO: 2 and wherein the variant has higher specific activity on ONPG as compared with a reference polypeptide having lactase activity (such as the polypeptide of SEQ ID NO: 2) and wherein said variant has at least 60% sequence identity with SEQ ID NO:2. Preferred is at least one substitution of an amino acid residue corresponding to any of amino acids 415 and/or 619 said position being defined with reference to SEQ ID NO: 2.

More preferably, the invention provides a variant polypeptide having lactase activity, wherein the variant has an amino acid sequence which, when aligned with the lactase comprising the sequence set out in SEQ ID NO: 2, comprises at least one substitution selected from T415C, T415A, A483S, V619I, I621V, M622L or T633G, said positions being defined with reference to SEQ ID NO: 2 and wherein the variant has higher specific activity on ONPG as compared with a reference polypeptide having lactase activity (such as the polypeptide of SEQ ID NO: 2) and wherein said variant has at least 60% sequence identity with SEQ ID NO:2. Preferred is substitution T415C and/or V619I said position being defined with reference to SEQ ID NO: 2.

Another variant polypeptide of the invention may demonstrate higher specific activity on lactose. Since lactose is the natural substrate in dairy products of lactase, a higher specific activity of the variant polypeptide can lead to a reduction of the required dosage of the enzyme and therefore may lead to a lower cost of the treatment. By reducing the enzyme dosage in the application also the amount of side activities added is reduced, and therefore a higher quality of the final dairy product is to be expected.

The invention thus provides a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids 233, 257, 258, 263, 274, 284, 297, 415, 440, 483, 619, 621, 622, 633, 862 or 1004 said positions being defined with reference to SEQ ID NO: 2 and wherein the variant has higher specific activity on lactose as compared with a reference polypeptide having lactase activity (such as the polypeptide of SEQ ID NO: 2) and wherein said variant has at least 60% sequence identity with SEQ ID NO:2.

Preferably, the invention provides a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids 415, 440 or 483 said positions being defined with reference to SEQ ID NO: 2 and wherein the variant has higher specific activity on lactose as compared with a reference polypeptide having lactase activity (such as the polypeptide of SEQ ID NO: 2) and wherein said variant has at least 60% sequence identity with SEQ ID NO:2. Preferred is at least one substitution of an amino acid residue corresponding to any of amino acids 415 and/or 483 (this preference is based on analysis of lactase variants comprising a combination of substitutions) said position being defined with reference to SEQ ID NO: 2.

More preferably, the invention provides a variant polypeptide having lactase activity, wherein the variant has an amino acid sequence which, when aligned with the lactase comprising the sequence set out in SEQ ID NO: 2, comprises at least one substitution selected from T415C, T415A, Y440F or A483S, said positions being defined with reference to SEQ ID NO: 2 and wherein the variant has higher specific activity on lactose as compared with a reference polypeptide having lactase activity (such as the polypeptide of SEQ ID NO: 2) and wherein said variant has at least 60% sequence identity with SEQ ID NO:2. Preferred is substitution T415A, T415C and/or A483S (this preference is based on analysis of lactase variants comprising a combination of substitutions) said position being defined with reference to SEQ ID NO: 2.

Even more preferably, the invention provides a variant polypeptide having lactase activity, wherein the variant has an amino acid sequence which, when aligned with the lactase comprising the sequence set out in SEQ ID NO: 2, comprises at least two, three, four or five substitutions of an amino acid residue corresponding to any of amino acids 233, 257, 258, 263, 274, 284, 297, 415, 440, 483, 619, 621, 622, 633, 862 or 1004 said positions being defined with reference to SEQ ID NO: 2 and wherein the variant has higher specific activity on lactose as compared with a reference polypeptide having lactase activity (such as the polypeptide of SEQ ID NO: 2) and wherein said variant has at least 60% sequence identity with SEQ ID NO:2.

Examples of such mutants are mutants 16, 17, 18, 20, 21, 22, 23, 24, 25, 26, 27, 28, 29, 30, 31, 32, 33, 34, 35 or 36 as described in Table 5.

Yet another variant polypeptide of the invention may demonstrate higher activity on lactose in milk, preferably at low temperatures (preferably said low temperatures are in the range of 4-12° C.). Since often lactases are used in milk at a low temperature, an increased activity of the variant polypeptide in this specific application may lead to the reduction of the enzyme dosage, and hence reduce the costs. Additionally, a higher activity of the variant polypeptide may lead to a reduction in the processing time of milk and therefore reduce the risk for possible microbial spoilage.

The invention thus provides a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids 233, 257, 258, 263, 274, 284, 297, 415, 440, 483, 619, 621, 622, 633, 862 or 1004 said positions being defined with reference to SEQ ID NO: 2 and wherein the variant demonstrates increased activity on lactose in milk at a low temperature as compared with a reference polypeptide having lactase activity (such as the polypeptide of SEQ ID NO: 2) and wherein said variant has at least 60% sequence identity with SEQ ID NO:2.

Preferably, the invention provides a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids 233, 257, 258, 263, 274, 284, 297, 440, 619, 633, 862 or 1004 said positions being defined with reference to SEQ ID NO: 2 and wherein the variant demonstrates increased activity on lactose in milk at a low temperature as compared with a reference polypeptide having lactase activity (such as the polypeptide of SEQ ID NO: 2) and wherein said variant has at least 60% sequence identity with SEQ ID NO:2. Preferred is a substitution of (at least) an amino acid residue corresponding to amino acid 440 said position being defined with reference to SEQ ID NO: 2 (this preference is based on analysis of lactase variants comprising a combination of substitutions). A preferred combination of substitutions is a substitution at position 440 and 619.

More preferably, the invention provides a variant polypeptide having lactase activity, wherein the variant has an amino acid sequence which, when aligned with the lactase comprising the sequence set out in SEQ ID NO: 2, comprises at least one substitution selected from D233V, D257G, A258T, N263S, K274E, N284S, E297G, Y440F, V619I, T633G, L862V or A1004P said positions being defined with reference to SEQ ID NO: 2 and wherein the variant demonstrates increased activity on lactose in milk at a low temperature as compared with a reference polypeptide having lactase activity (such as the polypeptide of SEQ ID NO: 2) and wherein said variant has at least 60% sequence identity with SEQ ID NO:2. Preferred is a substitution of (at least) Y440F said position being defined with reference to SEQ ID NO: 2 (this preference is based on analysis of lactase variants comprising a combination of substitutions). A preferred combination of substitutions is Y440F+V619I.

Although, the presence of at least one substitution of an amino acid residue corresponding to any of amino acids 233, 257, 258, 263, 274, 284, 297, 440, 619, 633, 862 or 1004 said positions being defined with reference to SEQ ID NO: 2 is sufficient to obtain a variant polypeptide having lactase activity and further showing increased activity on lactose in milk at a low temperature, it is herein shown that also double or triple mutated polypeptide variants demonstrate increased activity on lactose in milk at a low temperature.

As a result the invention also provides a variant polypeptide having lactase activity, wherein the variant has an amino acid sequence which, when aligned with the lactase comprising the sequence set out in SEQ ID NO: 2, which comprises an amino acid sequence which, when aligned with the sequence set out in SEQ ID NO:2, comprises at least two substitutions selected from 263, 274 or 284 (more preferably N263S, K274E or N284S) said positions being defined with reference to SEQ ID NO: 2 and wherein the variant demonstrates increased activity on lactose in milk at a low temperature as compared with a reference polypeptide having lactase activity (such as the polypeptide of SEQ ID NO: 2) and wherein said variant has at least 60% sequence identity with SEQ ID NO:2.

The invention further provides a variant polypeptide having lactase activity, wherein the variant has an amino acid sequence which, when aligned with the lactase comprising the sequence set out in SEQ ID NO: 2, which comprises an amino acid sequence which, when aligned with the sequence set out in SEQ ID NO:2, comprises substitutions at positions 263, 274 and 284 (preferably said substitutions are N263S, K274E and N284S)

said positions being defined with reference to SEQ ID NO: 2 and wherein the variant demonstrates increased activity on lactose in milk at a low temperature as compared with a reference polypeptide having lactase activity (such as the polypeptide of SEQ ID NO: 2) and wherein said variant has at least 60% sequence identity with SEQ ID NO:2.

The invention further provides a variant polypeptide having lactase activity, wherein the variant has an amino acid sequence which, when aligned with the lactase comprising the sequence set out in SEQ ID NO: 2, which comprises an amino acid sequence which, when aligned with the sequence set out in SEQ ID NO:2, comprises comprises an amino acid sequence which, when aligned with the sequence set out in SEQ ID NO:2, comprises substitutions at positions 257 and 297 (preferably said substitutions are D257G and E297G), said positions being defined with reference to SEQ ID NO: 2 and wherein the variant demonstrates increased activity on lactose in milk at a low temperature as compared with a reference polypeptide having lactase activity (such as the polypeptide of SEQ ID NO: 2) and wherein said variant has at least 60% sequence identity with SEQ ID NO:2.

The invention also provides a variant polypeptide having lactase activity, wherein the variant has an amino acid sequence which, when aligned with the lactase comprising the sequence set out in SEQ ID NO: 2, comprises at least three, four of five substitutions of an amino acid residue corresponding to any of amino acids 233, 257, 258, 263, 274, 284, 297, 415, 440, 483, 619, 621, 622, 633, 862 or 1004 said positions being defined with reference to SEQ ID NO: 2 and wherein the variant demonstrates increased activity on lactose in milk at a low temperature as compared with a reference polypeptide having lactase activity (such as the polypeptide of SEQ ID NO: 2) and wherein said variant has at least 60% sequence identity with SEQ ID NO:2.

Examples of such mutants are mutants 15, 17, 18, 19, 20, 21 or 22 as described in Table 5.

Yet a further variant polypeptide of the invention may demonstrate a reduction in galactose inhibition. Galactose inhibition leads to slow hydrolysis of lactose at later time points, when the lactose concentration is low, and the galactose concentration is high. It would thus be desirable to have a lactase enzyme which has reduced galactose inhibition, especially when one wishes to produce a dairy product where the lactose concentration is lower than 0.5 g/L.

The invention thus provides a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids 233, 257, 258, 263, 274, 284, 297, 415, 440, 483, 619, 621, 622, 633, 862 or 1004 said positions being defined with reference to SEQ ID NO: 2 and wherein the variant demonstrates decreased galactose inhibition as compared with a reference polypeptide having lactase activity (such as the polypeptide of SEQ ID NO: 2) and wherein said variant has at least 60% sequence identity with SEQ ID NO:2.

Preferably, the invention provides a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids 619, 621 or 622 said positions being defined with reference to SEQ ID NO: 2 and wherein the variant demonstrates decreased galactose inhibition as compared with a reference polypeptide having lactase activity (such as the polypeptide of SEQ ID NO: 2) and wherein said variant has at least 60% sequence identity with SEQ ID NO:2.

More preferably, the invention provides a variant polypeptide having lactase activity, wherein the variant has an amino acid sequence which, when aligned with the lactase comprising the sequence set out in SEQ ID NO: 2, comprises at least one substitution selected from V619I, I621V or M622L said positions being defined with reference to SEQ ID NO: 2 and wherein the variant demonstrates decreased galactose inhibition as compared with a reference polypeptide having lactase activity (such as the polypeptide of SEQ ID NO: 2) and wherein said variant has at least 60% sequence identity with SEQ ID NO:2.

Yet a further variant polypeptide of the invention may demonstrate increased GOS production in milk. GOS (galacto-oligosaccharides) are prebiotics which are defined as non-digestible food ingredients that beneficially affect the host by stimulating the growth and/or activity of beneficial bacteria in the colon. Not all lactases are equally well suited for preparing GOS. It would be desired to have another lactase enzyme which is capable of accumulation of GOS at the low lactose concentration that is present in milk (<50 g/L).

The invention thus provides a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids 233, 257, 258, 263, 274, 284, 297, 415, 440, 483, 619, 621, 622, 633, 862 or 1004 said positions being defined with reference to SEQ ID NO: 2 and wherein the variant demonstrates increased GOS production in milk as compared with a reference polypeptide having lactase activity (such as the polypeptide of SEQ ID NO: 2) and wherein said variant has at least 60% sequence identity with SEQ ID NO:2.

Preferably, the invention provides a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids 619 or 622 said positions being defined with reference to SEQ ID NO: 2 and wherein the variant demonstrates increased GOS production in milk as compared with a reference polypeptide having lactase activity (such as the polypeptide of SEQ ID NO: 2) and wherein said variant has at least 60% sequence identity with SEQ ID NO:2.

More preferably, the invention provides a variant polypeptide having lactase activity, wherein the variant has an amino acid sequence which, when aligned with the lactase comprising the sequence set out in SEQ ID NO: 2, comprises at least one substitution selected from V619I or M622L said positions being defined with reference to SEQ ID NO: 2 and wherein the variant demonstrates increased GOS production in milk as compared with a reference polypeptide having lactase activity (such as the polypeptide of SEQ ID NO: 2) and wherein said variant has at least 60% sequence identity with SEQ ID NO:2.

A variant lactase of the invention may also comprise additional modifications in comparison to the parent at positions other than those specified above, for example, one or more additional substitutions, additions or deletions. A variant of the invention may comprise a combination of different types of modification of this sort. A variant may comprise one, two, three, four, at least 5, at least 10, at least 15, at least 20, at least 25, at least 30 or more such modifications (which may all be of the same type or may be different types of modification). Typically, the additional modifications may be substitutions. The invention thus also provides a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids 233, 257, 258, 263, 274, 284, 297, 415, 440, 483, 619, 621, 622, 633, 862 or 1004 said positions being defined with reference to SEQ ID NO: 2 and wherein the variant has one or more altered properties as compared with a reference polypeptide having lactase activity and wherein said variant polypeptide comprises additional substitutions other than those defined and wherein said variant has at least 60% sequence identity with SEQ ID NO:2.

A variant according to the invention (for example a variant having one or more substitution as set out in Table 1 or Table 2) may have at least about 60%, 65%, 70%, 75% or 80% homology/identity with the reference lactase polypeptide, such as the lactase of SEQ ID NO: 2, for example at least about 85% homology with the parent polypeptide, such as least about 90% homology with the parent polypeptide, at least 95% homology with the parent polypeptide, at least about 98% homology with the parent polypeptide or at least about 99% homology with the parent polypeptide. Such a variant will typically have one or more substitution or sets of substitutions as set out in Table 1 or Table 2.

The invention thus also provides a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids 233, 257, 258, 263, 274, 284, 297, 415, 440, 483, 619, 621, 622, 633, 862 or 1004 said positions being defined with reference to SEQ ID NO: 2 and wherein the variant has one or more altered properties as compared with a reference polypeptide having lactase activity and wherein said variant has at least 80% sequence identity with SEQ ID NO:2.

A variant of the invention will typically retain lactase activity. That is to say, a variant of the invention will typically be capable of converting lactose to glucose and galactose or a variant of the invention will typically be capable of converting lactose to glucose and galactose and capable of forming GOS. A variant of the invention is one which is typically capable of performing an enzymatic conversion of lactose and which may be used in the preparation of a dairy product, such as a milk or yoghurt.

Preferably, a variant of the invention will typically exhibit improved properties in comparison with the reference lactase polypeptide from which it is derived. Such an improved property will typically be one which is relevant if the variant were to be used as set out below, for example in a method for preparing a dairy product.

A polypeptide variant which exhibits a property which is improved in relation to the reference lactase is one which demonstrates a measurable reduction or increase in the relevant property, typically such that the variant is more suited to use as set out below, for example in a method for the production of a dairy product.

The property may thus be decreased by at least 10%, at least 20%, at least 30%, at least 40% at least 50%, at least 60%, at least 70%, at least 80%, at least 90%, at least 95% or at least 99%. Alternatively, the property may be increased by at least 10%, at least 25%, at least 50%, at least 100%, at least, 200%, at least 500% or at least 1000%. The percentage decrease or increase in this context represents the percentage decrease or increase in comparison to the reference lactase polypeptide. It is well known to the skilled person how such percentage changes may be measured—it is a comparison of the activity of the reference lactase and the variant lactase.

The variants described herein are collectively comprised in the terms "a polypeptide according to the invention" or "a variant according to the invention".

The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than about seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989).

A polypeptide of the invention may be in isolated form, such as substantially isolated form. By "isolated" polypeptide or protein is intended a polypeptide or protein removed from its native environment. For example, recombinantly produced polypeptides and proteins expressed in host cells are considered isolated for the purpose of the invention as are recombinant polypeptides which have been substantially purified by any suitable technique. A polypeptide variant according to the invention can be recovered and purified from recombinant cell cultures by methods known in the art.

Polypeptides of the present invention include products of chemical synthetic procedures, and products produced by recombinant techniques from a prokaryotic or eukaryotic host, including, for example, bacterial, yeast, fungal, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The invention also features biologically active fragments of the polypeptide variants according to the invention. Such fragments are considered to be encompassed within the term "a variant of the invention".

Biologically active fragments of a polypeptide variant of the invention include polypeptides comprising amino acid sequences sufficiently identical to or derived from the amino acid sequence of a variant protein of the invention which include fewer amino acids than the full length protein but which exhibit at least one biological activity of the corresponding full-length protein. Typically, biologically active fragments comprise a domain or motif with at least one activity of a variant protein of the invention. A biologically active fragment of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the invention.

Typically, a protein fragment of the invention will comprise one or more of the substitutions defined herein.

The invention also features nucleic acid fragments which encode the above biologically active fragments (which biologically active fragments are themselves variants of the invention).

The present invention also provides a nucleic acid sequence encoding the variant polypeptides of the invention. The invention thus also provides a nucleic acid sequence encoding a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids 233, 257, 258, 263, 274, 284, 297, 415, 440, 483, 619, 621, 622, 633, 862 or 1004 said positions being defined with reference to SEQ ID NO: 2 and wherein the variant has one or more altered properties as compared with a reference polypeptide having lactase activity (such as the polypeptide of SEQ ID NO: 2) and wherein said variant has at least 60% sequence identity with SEQ ID NO:2.

The invention also relates to an isolated polynucleotide encoding at least one functional domain of a polypeptide variant of the invention. Typically, such a domain will comprise one or more of the substitutions described herein.

In one embodiment of the invention, the nucleic acid sequence according to the invention encodes a polypeptide, wherein the polypeptide is a variant comprising an amino acid sequence that has one or more truncation(s), and/or at least one substitution, deletion and/or insertion of an amino acid as compared to the parent lactase. Such a polypeptide will, however, typically comprise one or more of the substitutions described herein.

As used herein, the terms "gene" and "recombinant gene" refer to nucleic acid molecules which include an open reading frame encoding a variant as described herein. A gene may include coding sequences, non-coding sequences, introns and regulatory sequences. That is to say, a "gene", as used herein, may refer to an isolated nucleic acid molecule as defined herein. Accordingly, the term "gene", in the context of the present application, does not refer only to naturally-occurring sequences.

A nucleic acid molecule of the present invention can be generated using standard molecular biology techniques well known to those skilled in the art taken in combination with the sequence information provided herein.

For example, using standard synthetic techniques, the required nucleic acid molecule may be synthesized de novo. Such a synthetic process will typically be an automated process.

Alternatively, a nucleic acid molecule of the invention may be generated by use of site-directed mutagenesis of an existing nucleic acid molecule, for example a wild-type nucleic acid molecule. Site-directed mutagenesis may be carried out using a number of techniques well known to those skilled in the art.

In one such method, mentioned here merely by way of example, PCR is carried out on a plasmid template using oligonucleotide "primers" encoding the desired substitution. As the primers are the ends of newly-synthesized strands, should there be a mis-match during the first cycle in binding the template DNA strand, after that first round, the primer-based strand (containing the mutation) would be at equal concentration to the original template. After successive cycles, it would exponentially grow, and after 25, would outnumber the original, unmutated strand in the region of 8 million:1, resulting in a nearly homogeneous solution of mutated amplified fragments. The template DNA may then be eliminated by enzymatic digestion with, for example using a restriction enzyme which cleaves only methylated DNA, such as Dpn1. The template, which is derived from an alkaline lysis plasmid preparation and therefore is methylated, is destroyed in this step, but the mutated plasmid is preserved because it was generated in vitro and is unmethylated as a result.

In such a method more than one mutation (encoding a substitution as described herein) may be introduced into a nucleic acid molecule in a single PCR reaction, for example by using one or more oligonucleotides, each comprising one or more mis-matches. Alternatively, more than one mutation may be introduced into a nucleic acid molecule by carrying out more than one PCR reaction, each reaction introducing one or more mutations, so that altered nucleic acids are introduced into the nucleic acid in a sequential, iterative fashion.

A nucleic acid of the invention can be generated using cDNA, mRNA or alternatively, genomic DNA, as a template and appropriate mis-matched oligonucleotide primers according to the site-directed mutagenesis technique described above. A nucleic acid molecule derived in this way can be cloned into an appropriate vector and characterized by DNA sequence analysis.

A nucleic acid sequence of the invention may comprise one or more deletions, i.e. gaps, in comparison to the parent lactase. Such deletions/gaps may also be generated using site-directed mutagenesis using appropriate oligonucleotides. Techniques for generating such deletions are well known to those skilled in the art.

Furthermore, oligonucleotides corresponding to or hybridizable to nucleotide sequences according to the invention can be prepared by standard synthetic techniques, e.g., using an automated DNA synthesizer.

Also, complementary nucleic acid molecules are included in the present invention. A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a variant of the invention, or a biologically active fragment or domain thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules, such as for the preparation of nucleic acid molecules of the invention.

An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Another embodiment of the invention provides an isolated nucleic acid molecule which is antisense to a nucleic acid molecule of the invention.

The terms "homology" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at www.accclrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at www.ncbi.nlm.nih.gov.

The invention further provides a nucleic acid construct comprising a nucleic acid sequence encoding a variant polypeptide having lactase activity, wherein the variant has an amino acid sequence which, when aligned with the lactase comprising the sequence set out in SEQ ID NO: 2, comprises at least one substitution of an amino acid residue corresponding to any of amino acids 233, 257, 258, 263, 274, 284, 297, 415, 440, 483, 619, 621, 622, 633, 862 or 1004 said positions being defined with reference to SEQ ID NO: 2 and wherein the variant has one or more altered properties as compared with a reference polypeptide having lactase activity (such as the polypeptide of SEQ ID NO: 2) and wherein said variant has at least 60% sequence identity with SEQ ID NO:2, wherein said nucleic acid sequence is operably linked to one or more control sequences capable of directing the expression of a lactase in a suitable expression host cell.

Another aspect of the invention pertains to vectors, preferably expression vectors, containing a nucleic acid encoding a variant lactase polypeptide of the invention.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signal). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, encoded by nucleic acids as described herein (e.g. a lactase variant of SEQ ID NO: 2, for example a functional equivalent or fragment, or a fusion protein comprising one or more of such variants).

The recombinant expression vectors of the invention can be designed for expression of variant proteins of the invention in prokaryotic or eukaryotic cells. For example, a variant protein of the invention can be expressed in bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The DNA insert should be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled person. In a specific embodiment, promoters are preferred that are capable of directing a high expression level of lactase in filamentous fungi. Such promoters are known in the art. The expression constructs may contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, transduction, infection, lipofection, cationic lipidmediated transfection or electroporation. Suitable methods for transforming or transfecting host cells can be found in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989), Davis et al., Basic Methods in Molecular Biology (1986) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methatrexate. Nucleic acid encoding a selectable marker can be introduced into a host cell on the same vector as that encoding a variant protein of the invention or can be introduced on a separate vector. Cells stably transfected with the introduced nucleic acid can be identified by drug selection (e.g. cells that have incorporated the selectable marker gene will survive, while the other cells die).

Expression of proteins in prokaryotes is often carried out in *E. coli* with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein.

As indicated, the expression vectors will preferably contain selectable markers. Such markers include dihydrofolate reductase or neomycin resistance for eukaryotic cell culture and tetracycline or ampicillin resistance for culturing in *E. coli* and other bacteria. Representative examples of appropriate host include bacterial cells, such as *E. coli, Streptomyces, Salmonella typhimurium* and certain *Bacillus* species, such as *B. subtilis, B. amyloliquefaciens, B. licheniformis*, and *B. clausii*; fungal cells such as *Aspergillus* species, for example *A. niger, A. oryzae* and *A. nidulans*, and/or *Fusarium* species such as *F. venenatum*, and/or *Trichoderma* species, such as *T. reesei*; yeast cells such as *Kluyveromyces*, for example *K. lactis* and *K. marxianus* and/or *Pichia*, for example *P. pastoris*, and/or *Saccharomyces*, for example *S. cerevisiae*, and/or *Hansenula*, for example *H. polymorpha*; insect cells such as *Drosophila* S2 and *Spodoptera* Sf9; animal cells such as CHO, COS and Bowes melanoma; and plant cells. Appropriate culture mediums and conditions for the above-described host cells are known in the art.

Vectors preferred for use in bacteria are for example disclosed in WO-A1-2004/074468, which are hereby enclosed by reference. Other suitable vectors will be readily apparent to the skilled artisan.

Known bacterial promoters suitable for use in the present invention include the promoters disclosed in WO-A1-2004/074468, which are hereby incorporated by reference.

Transcription of the DNA encoding a variant of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signal may be incorporated into the expressed polypeptide. The signals may be endogenous to the polypeptide or they may be heterologous signals.

A variant of the invention may be expressed in form such that it may include additional heterologous functional regions, for example secretion signals. A variant of the invention may also comprise, for example, a region of additional amino acids, particularly charged amino acids, added to the N-terminus of the polypeptide for instance to improve stability and persistence in the host cell, during purification or during subsequent handling and storage. Also, peptide moieties may be added to a variant of the invention to facilitate purification, for example by the addition of histidine residues or a T7 tag.

The variants of the invention, such as proteins of the present invention or functional equivalents thereof, e.g., biologically active portions and fragments thereof, can be operatively linked to a non-variant polypeptide (e.g., heterologous amino acid sequences) to form fusion proteins. A "non-variant polypeptide" in this context refers to a polypeptide having an amino acid sequence corresponding to a protein which is not substantially homologous to a variant lactase of the invention.

Within a fusion protein, the variant of the invention can correspond to a full length sequence or a biologically active fragment of a polypeptide of the invention. In a preferred embodiment, a fusion protein of the invention comprises at least two biologically active portions. Within the fusion protein, the term "operatively linked" is intended to indicate that the variant polypeptide and the non-variant polypeptide are fused in-frame to each other. The non-variant polypeptide can be fused to the N-terminus or C-terminus of the variant polypeptide.

Expression and secretion of a variant lactase may be enhanced by expressing the variant in the form of a fusion protein. In this context, a nucleic acid sequence may encode for a fusion protein comprising lactase. More specifically, the fusion partner may be glucoamylase or a fragment thereof. In one embodiment the lactase, or a fusion protein thereof, is secreted over the host cell membrane.

For example, in one embodiment, the fusion protein is a fusion protein in which the variant sequence/s is/are fused to the C-terminus of the GST sequences. Such fusion proteins can facilitate the purification of a recombinant variant according to the invention. In another embodiment, the fusion protein is a variant of the invention containing a heterologous signal sequence at its N-terminus. In certain host cells (e.g., mammalian and yeast host cells), expression and/or secretion of a variant of the invention can be increased through use of a heterologous signal sequence.

In another example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokarytic heterologous signal sequences include the phoA secretory signal (Sambrook et al., supra) and the protein A secretory signal (Pharmacia Biotech; Piscataway, N.J.).

A signal sequence can be used to facilitate secretion and isolation of a variant of the invention. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. The signal sequence may direct secretion of the variant, such as from a eukaryotic host into which the expression vector is transformed, and the signal sequence may then be subsequently or concurrently cleaved. The variant of the invention may then be readily purified from the extracellular medium by known methods. Alternatively, the signal sequence can be linked to the variant of interest using a sequence, which facilitates purification, such as with a GST domain. Thus, for instance, the sequence encoding the variant of the invention may be fused to a marker sequence, such as a sequence encoding a peptide, which facilitates purification of the fused variant of the invention. In certain preferred embodiments of this aspect of the invention, the marker sequence is a hexa-histidine peptide, such as the tag provided in a pQE vector (Qiagen, Inc.), among others, many of which are commercially available. As described in Gentz et al, Proc. Natl. Acad. Sci. USA 86:821-824 (1989), for instance, hexa-histidine provides for convenient purification of the fusion protein. The HA tag is another peptide useful for purification which corresponds to an epitope derived of influenza hemaglutinin protein, which has been described by Wilson et al., Cell 37:767 (1984), for instance.

A fusion protein of the invention may be produced by standard recombinant DNA techniques. For example, DNA fragments coding for the different polypeptide sequences are ligated together in frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers, which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g, a GST polypeptide). A variant-encoding nucleic acid can be cloned into such an expression vector such that the fusion moiety is linked in-frame to the said variant.

The terms "functional equivalents" and "functional variants" are used interchangeably herein. Functional equivalents according to the invention are isolated DNA fragments that encode a polypeptide that exhibits a particular function of a variant as defined herein. Functional equivalents therefore also encompass biologically active fragments and are themselves encompassed within the term "a variant" of the invention.

Preferably, a functional equivalent of the invention comprises one or more of the substitutions described herein. However, a functional equivalent may comprise one or more modifications in addition to the substitutions described above.

Functional nucleic acid equivalents may typically contain silent mutations or mutations that do not alter the biological function of encoded polypeptide. Accordingly, the invention provides nucleic acid molecules encoding a variant lactase protein that contains changes in amino acid residues that are not essential for a particular biological activity. Such variant proteins differ in amino acid sequence from the parent lactase sequence from which they are derived yet retain at least one biological activity thereof, preferably they retain at least lactase activity. In one embodiment the isolated nucleic acid molecule comprises a nucleotide sequence encoding a protein, wherein the protein comprises a substantially homologous amino acid sequence of at least about 60%, 65%, 70%, 75%, 80%, 85%, 90%, 95%, 96%, 97%, 98%, 99% or more homologous to the reference amino acid sequence (for example that shown in SEQ ID NO: 2).

As defined herein, the term "substantially homologous" refers to a first amino acid or nucleotide sequence which contains a sufficient or minimum number of identical or equivalent (e.g., with similar side chain) amino acids or nucleotides to a second amino acid or nucleotide sequence such that the first and the second amino acid or nucleotide sequences have a common domain. For example, amino acid or nucleotide sequences which contain a common domain having about 60%, preferably 65%, more preferably 70%, even more preferably 75%, 80%, 85%, 90%, 95%, 96%, 97%, 98% or 99% identity or more are defined herein as sufficiently identical.

The skilled person will recognise that changes can be introduced by mutation into the nucleotide sequences according to the invention thereby leading to changes in the amino acid sequence of the resulting protein without substantially altering the function of such a protein.

Accordingly, a lactase variant of the invention is preferably a protein which comprises an amino acid sequence at least about 60%, 65%, 70%, 75%, 80%, 85%, 90%, 95%, 96%, 97%, 98%, 99% or more homologous to the reference amino acid sequence, for example that shown in SEQ ID NO: 2, and typically also retains at least one functional activity of the reference polypeptide. Variants of the invention, for example functional equivalents of a protein according to the invention, can also be identified e.g. by screening combinatorial libraries of mutants, e.g. truncation mutants, of the protein of the invention for lactase activity. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g. for phage display). There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198: 1056; Ike et al. (1983) Nucleic Acid Res. 11:477).

In addition, libraries of fragments of the sequence encoding a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3): 327-331).

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides can be used as hybridization probes or polymerase chain reaction (PCR) primers. Uses of the nucleic acid molecules of the present invention that do not encode a polypeptide having lactase activity include, inter alia, (1) in situ hybridization (e.g. FISH) to metaphase chromosomal spreads to provide precise chromosomal location of an lactase-encoding gene as described in Verma et al., Human Chromosomes: a Manual of Basic Techniques, Pergamon Press, New York (1988); (2) Northern blot analysis for detecting expression of lactase mRNA in specific tissues and/or cells; and (3) probes and primers that can be used as a diagnostic tool to analyse the presence of a nucleic acid hybridizable to such a probe or primer in a given biological (e.g. tissue) sample.

Variants of a given reference lactase enzyme can be obtained by the following standard procedure:

Mutagenesis (error-prone, doped oligo, spiked oligo) or synthesis of variants
  Transformation in, for example *E. coli* or *K. lactis*
  Cultivation of transformants, selection of transformants
  Expression
  Optional purification and concentration
  Primary Screening
  Identification of an improved variant (for example in relation to specific activity)

In one embodiment the invention relates to a method of producing a lactase polypeptide variant according to the invention, which method comprises:
  a) selecting a reference lactase polypeptide;
  b) substituting at least one amino acid residue corresponding to any of
    233, 257, 258, 263, 274, 284, 297, 415, 440, 483, 619, 621, 622, 633, 862 or 1004
    said positions being defined with reference to SEQ ID NO: 2;
  c) optionally substituting one or more further amino acids as defined in b);
  d) preparing the variant resulting from steps a)-c);
  e) determining a property of the variant, for example as set out in the Examples; and
  f) selecting a variant having an altered property in comparison to the reference lactase polypeptide and wherein said variant has at least 60% sequence identity with SEQ ID NO:2.

In a preferred embodiment in the method of producing a lactase polypeptide variant according to the invention, the reference lactase polypeptide has the sequence set out in SEQ ID NO: 2.

More preferably in step b) of the method according to the invention at least one amino acid residue corresponding to any of
    233, 257, 258, 263, 274, 284, 297, 415, 440, 483, 619, 621, 622, 633, 862 or 1004
is substituted, said positions being defined with reference to SEQ ID NO: 2. The reference polypeptide may have at least about 80% homology with SEQ ID NO: 2.

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are cells from yeasts, for example, *K. lactis*. Host cells also include, but are not limited to, mammalian cell lines such as CHO, VERO, BHK, HeLa, COS, MDCK, 293, 3T3, W138, and choroid plexus cell lines.

Examples of suitable bacterial host organisms are gram positive bacterial species such as Bacillaceae including *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium* and *Bacillus thuringiensis, Streptomyces* species such as *Streptomyces murinus*, lactic acid bacterial species including *Lactococcus* spp. such as *Lactococcus lactis, Lactobacillus* spp. including *Lactobacillus reuteri, Leuconostoc* spp. and *Streptococcus* spp. Alternatively, strains of a gram negative bacterial species such as a species belonging to Enterobacteriaceae, including *E. coli* or to Pseudomonadaceae may be selected as the host organism.

A suitable yeast host organism may advantageously be selected from a species of *Saccharomyces* including *Saccharomyces cerevisiae* or a species belonging to *Schizosaccharomyces*. Further useful yeast host organisms include *Pichia* spp. such as methylotrophic species hereof, including *Pichia pastoris*, and *Kluyveromyces* spp. including *Kluyveromyces lactis*.

Suitable host organisms among filamentous fungi include species of *Acremonium, Aspergillus, Fusarium, Humicola, Mucor, Myceliophtora, Neurospora, Penicillium, Thielavia, Tolypocladium* or *Trichoderma*, such as e. g. *Aspergillus aculeatus, Aspergillus awamori, Aspergillus foetidus, Aspergillus japonicus, Aspergillus oryzae, Aspergillus nidulans* or *Aspergillus niger*, including *Aspergillus* nigervar. awamori, *Fusarium bactridioides, Fusarium cereals, Fusarium crookwellense, Fusarium culmorum, Fusarium graminearum,*

Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichiodes, Fusarium sulphureum, Fusarium torulosum, Fusarium trichothecioides, Fusarium venenatum, Humicola insolens, Humicola languinosa, Mucor miehei, Myceliophtora thermophila, Neurospora crassa, Penicillium chrysogenum, Penicillium camenbertii, Penicillium purpurogenum, Rhizomucor miehei, Thielavia terestris, Trichoderma harzianum, Trichoderma koningii, Trichoderma longibrachiatum, Trichoderma reesii or Trochoderma viride.

A host cell can be chosen that modulates the expression of the inserted sequences, or modifies and processes the product encoded by the incorporated nucleic acid sequence in a specific, desired fashion. Such modifications (e.g., glycosylation) and processing (e.g., cleavage) of protein products may facilitate optimal functioning of the encoded protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

If desired, a stably transfected cell line can produce a variant according to the invention. A number of vectors suitable for stable transfection of mammalian cells are available to the public, methods for constructing such cell lines are also publicly known, e.g., in Ausubel et al. (supra).

The present invention further discloses a composition comprising the lactase variants according to the invention. The invention thus provides a composition comprising the variant polypeptide as described herein and at least one component selected from salt (like sodium or potassium chloride), preservative, a polyol (like glycerol), metal ions (like magnesium or manganese ions).

The composition may optionally comprise other ingredients such as e.g. other enzymes. Such a composition may comprises the variant polypeptide of the invention or one obtainable by a method of the invention for identifying a variant lactase.

In addition to the variant lactase, and one or more additional enzymes, if present, a composition according to the invention may comprise additives that are conventionally used in lactase preparations such as e. g. KCl or glycerol.

The invention further relates to use of a variant polypeptide of the invention or a composition of the invention in the preparation of a dairy product.

The invention also relates to a process for the production of a dairy product, which method comprises comprising adding an effective amount of a variant polypeptide or a composition of the invention to milk and allowing the variant polypeptide to exerts its enzymatic activity.

The invention relates to a dairy product obtainable by such a process. As used herein, a dairy product encompasses any composition that is produced from milk, for instance casein and/or whey protein. Examples are milk, milk-derived products, fermented milk products (e.g. yoghurt), condensed milk, UHT milk, evaporated milk, powdered milk, frozen milk, ice cream, cream, butter, butter milk, whey; and/or cheese. The product may also be a hydrolysate or a product obtained by fractionation of milk or whey, like caseinate, milk protein concentrate, whey protein concentrate (WPC), whey protein isolate (WPI), or (concentrated) whey permeate and products made thereof The milk is for example obtained from cow, buffalo, goat, sheep, camel, donkey, horse, reindeer, moose or yak.

A reference herein to a patent document or other matter which is given as prior art is not to be taken as an admission that that document or matter was known or that the information it contains was part of the common general knowledge as at the priority date of any of the claims.

The invention will now be elucidated with reference to the following examples without however being limited thereto.

EXAMPLES

General Material and Methods
Molecular and Genetic Techniques
Standard genetic and molecular biology techniques are known in the art (e.g. Maniatis et al. "*Molecular cloning: a laboratory manual*" (1982) Cold Spring Harbor Laboratory, Cold Spring Harbor, N.Y.; Miller "*Experiments in molecular genetics*" (1972) Cold Spring Harbor Laboratory, Cold Spring Harbor, N.Y.; Sambrook and Russell "*Molecular cloning: a laboratory manual*" ($3^{rd}$ edition)" (2001) Cold Spring Harbor Laboratory, Cold Spring Harbor Laboratory Press; Ausubel "*Current protocols in molecular biology*" (1987) Green Publishing and Wiley Interscience, New York).

Plasmids and Strains
pBAD/HisA was obtained from Invitrogen™ (LifeTechnologies Corporation, Carlsbad, Calif., USA). The beta-galactosidase deficient strain *Escherichia coli* BW25113 (Δ(araD-araB)567, ΔlacZ4787(::rrnB-3), λ⁻, rph-1, Δ(rhaD-rhaB)568, hsdR514) (Datsenko K A, Wanner B L (2000) *Proc Natl Acad Sci* USA 97: 6640-6645) was used for the expression of the *Kluyveromyces lactis* beta-galactosidase variants.

Media
2×PY medium (16 g/l BD BBL™ Phytone™ Peptone, 10 g/l Yeast Extract, 5 g/l NaCl) was used for growth of *Escherichia coli*. Antibiotics (100 microgram/ml ampicillin) were supplemented to maintain plasmids. For induction of gene expression L-arabinose was used at 0.02% final concentration.

Example 1: DNA Constructs and Transformation

Synthetic DNA constructs were designed to start with a BbsI restriction site resulting in an NcoI compatible overhang and ending with a BbsI restriction site after the stop codon resulting in an HindIII compatible overhang. Internal BbsI restriction sites were removed in the design of the synthetic DNA construct. As an example, a DNA fragment encoding the wild type *K. lactis* beta-galactosidase sequence is listed as SEQ ID NO: 1. All variants were designed in a similar fashion and cloned as BbsI fragments in the NcoI/HindIII sites of expression vector pBAD/HisA.

Amino acid changes that were introduced in the 14 variants that are depicted in Table 2. Position of the change is indicated in comparison with the wild type *K. lactis* beta-galactosidase amino acid sequence (SEQ ID NO: 2). Some variants have multiple changes introduced into the amino acid sequence of the beta-galactosidase protein, like variant #8, and #7. A wild-type gene encoding the unchanged beta-galactosidase protein was also used in gene cloning and transformation and was later used to compare with enzymes made with the variant genes.

TABLE 2

Amino acid changes introduced in the protein sequence of K. lactis beta-galactosidase Aminoacids are depicted according to the single letter annotation

| Variant# | Mutations | | |
|---|---|---|---|
| 1 | T633G | | |
| 2 | Y440F | | |
| 3 | A483S | | |
| 4 | A1004P | | |
| 5 | A258T | | |
| 6 | D233V | | |
| 7 | N263S | K274E | N284S |
| 8 | D257G | E297G | |
| 9 | L862V | | |
| 10 | V619I | | |
| 11 | T415C | | |
| 12 | T415A | | |
| 13 | M622L | | |
| 14 | I621V | | |

Transformation of E. coli BW25113 was done using the Zymo Research Z-Competent™ E. coli transformation kit & buffer set (T3001). The transformed E. coli strains were plated on 2×PY agar plates containing 100 μg/ml ampicillin, 0.02% L-arabinose, and 40 μg/ml 5-bromo-4-chloro-3-indolyl-β-D-galactopyranoside (X-Gal), and incubated at 30° C. overnight.

X-gal is an analog of lactose, and hydrolyzed by the β-galactosidase enzyme. X-gal, when cleaved by β-galactosidase, yields galactose and 5-bromo-4-chloro-3-hydroxyindole. The latter then spontaneously dimerizes and is oxidized into 5,5'-dibromo-4,4'-dichloro-indigo, an intensely blue product which is insoluble. The plates were stored at 4° C. for at least 24 hours to allow blue color formation upon hydrolysis of X-Gal. As the wild type E. coli strain BW25113 lacks β-galactosidase activity due to deletion of the lac operon, formation of blue color confirmed active expression of the chosen β-galactosidase variant. Of each construct three blue color forming transformants were tested for β-galactosidase production using small scale 24 well cultivation (example 2), and the best producing transformant was selected for further enzyme characterization.

Example 2: Cultivation and Preparation of Beta-Galactosidase Enzyme Samples

The E. coli BW25113 transformants expressing a variant beta-galactosidase gene were replicated from the agar plates into 96 wide well plates (NUNC 267334, NUNC A/S, Roskilde, Denmark) with 200 μl 2*PY and 100 μg/ml ampicillin followed by an overnight incubation at 30° C., 550 rpm and 80% humidity in an INFORS HT Microtron shaker (Infors AG, Bottmingen, Switzerland). 15 μl from these precultures was used to inoculate 24 wells plates (AXYGPDW10ML24CLIDS, Axygen™, Corning, N.Y. 14831 USA) comprising 3 ml 2*PY with 100 μg/ml ampicillin. The 24 well plates were covered with a breathseal (6786051, greiner bio-one, Frickenhausen, Germany) and incubated at 30° C., 550 rpm and 80% humidity in an INFORS HT Microtron shaker until an optical density 600 nm of 0.4-0.6 was reached. Then, L-arabinose was added to a final concentration of 0.02% and the 24 well plates were further incubated for 20-24 hours at 20° C., 750 rpm and 80% humidity in the INFORS HT Microtron shaker. The 24 well plates were centrifuged for 10 minutes at 2750 rpm and 4° C. and supernatant was removed by decanting the plate. The cell pellets obtained were stored at −20° C. for at least 24 hours. The frozen cell pellets were resuspended in 1 ml extraction buffer (50 mM Tris-HCl pH 7.5, 0.2 mM MgSO4, 2 mg/ml lysozym, 0.1 mg/ml DNAse I, 1× Complete Protease inhibitor cocktail (EDTA free, Roche)) by use of a vortex, incubated at room temperature for 30 minutes followed by centrifugation for 10 minutes at 2750 rpm and 4° C. The supernatant comprising the overexpressed beta-galactosidase (Cell Free Extract, CFE) was formulated by addition of 1 volume of glycerol and used in the different activity assays.

Example 3: Determination of the Amount of Lactase Protein

The amount of lactase protein produced by E. coli was determined using HP-SEC (Thermo Scientific Dionex Ulti-Mate 3000 Rapid Separation). For this 2 μl of the cell-free extracts (CFE) of Example 1 were loaded on a BEH200, sec 1.7 μm 4.6×150 mm column (Waters). The mobile phase consisted of 100 mM of potassium phosphate buffer (pH 7.32) and was kept at a flow of 0.1 mL/min. The column temperature kept at 25° C., while the flow was set at 0.1 mL/min. Elution of protein was followed by measuring the absorbance at 280 nm. Since the lactase protein is larger than most other proteins in the CFE it was the first protein peak that was eluted from the column under these conditions. The area under this peak was calculated and quantified by comparison to a bovine serum albumin (BSA) standard. Results of this quantification are used for the calculation of the (specific) activity of the proteins as described in Examples 4-7.

TABLE 3A

Results of the analysis of the (specific) activity of the variants in the various assays described in Examples 4-7. Values that are significantly (p < 0.05) higher or lower (% inhibition) from the average of wild-type lactases (6 samples) are marked.

| Variant | Mutation | Specific Activity_NLU/mg lactase Example 4 | Specific Activity_LACU/mg lactase Example 5 | Specific Activity_LACGU/mg lactase Example 6 | Inhibition % Examples 5 vs. 6 | milk:mg glucose/mg lactase in 4 h Example 7 | milk:mg/l GOS after 48 h Example 7 |
|---|---|---|---|---|---|---|---|
| 1 | T633G | 81 | 105 | 27 | 75 | 352 | 1209 |
| 2 | Y440F | 28 | 160 | 39 | 76 | 279 | 977 |
| 3 | A483S | 79 | 175 | 42 | 76 | 205 | 1494 |
| 4 | A1004P | 63 | 100 | 25 | 75 | 253 | 1062 |
| 5 | A258T | 66 | 98 | 29 | 71 | 305 | 1076 |
| 6 | D233V | 67 | 97 | 26 | 74 | 285 | 1026 |

TABLE 3A-continued

Results of the analysis of the (specific) activity of the variants in the
various assays described in Examples 4-7. Values that are significantly (p < 0.05) higher or
lower (% inhibition) from the average of wild-type lactases (6 samples) are marked.

| Variant | Mutation | | | Specific Activity_NLU/mg lactase Example 4 | Specific Activity_LACU/mg lactase Example 5 | Specific Activity_LACGU/mg lactase Example 6 | Inhibition % Examples 5 vs. 6 | milk:mg glucose/mg lactase in 4 h Example 7 | milk:mg/l GOS after 48 h Example 7 |
|---|---|---|---|---|---|---|---|---|---|
| 7 | N263S | K274E | N284S | 60 | 91 | 25 | 72 | 290 | 964 |
| 8 | D257G | E297G | | 71 | 99 | 28 | 72 | 256 | 1201 |
| 9 | L862V | | | 73 | 100 | 27 | 73 | 258 | 1269 |
| 10 | V619I | | | 79 | 75 | 23 | 69 | 300 | 2050 |
| 11 | T415C | | | 98 | 147 | 35 | 77 | 179 | 1436 |
| 12 | T415A | | | 78 | 169 | 37 | 78 | 164 | 1341 |
| 13 | M622L | | | 78 | 43 | 16 | 62 | 186 | 1818 |
| 14 | I621V | | | 76 | 40 | 19 | 52 | 99 | 616 |
| average | wild-type | | | 67 | 103 | 28 | 73 | 206 | 1277 |
| st. dev. | | | | 4 | 10 | 1 | 2 | 12 | 164 |

TABLE 3B

Results of the analysis of the (specific) activity of the variants in the
various assays described in Examples 4-7. The values of Table 3A are expressed
relative values compared to the values of the wild type enzyme in the sam assay.

| Variant | Mutation | | | Relative Specific Activity NLU/mg lactase Example 4 | Relative Specific Activity LACU/mg lactase Example 5 | Relative Specific Activity LACGU/mg lactase Example 6 | Relative Inhibition Examples 5 vs. 6 | relative activity in milk Example 7 | relative GOS production in milk Example 7 |
|---|---|---|---|---|---|---|---|---|---|
| 1 | T633G | | | 120 | 102 | 97 | 102 | 171 | 95 |
| 2 | Y440F | | | 42 | 155 | 140 | 104 | 135 | 77 |
| 3 | A483S | | | 117 | 169 | 152 | 104 | 99 | 117 |
| 4 | A1004P | | | 94 | 97 | 92 | 102 | 122 | 83 |
| 5 | A258T | | | 98 | 95 | 104 | 97 | 148 | 84 |
| 6 | D233V | | | 100 | 94 | 93 | 101 | 138 | 80 |
| 7 | N263S | K274E | N284S | 90 | 88 | 92 | 99 | 141 | 75 |
| 8 | D257G | E297G | | 106 | 96 | 100 | 99 | 124 | 94 |
| 9 | L862V | | | 109 | 96 | 98 | 100 | 125 | 99 |
| 10 | V619I | | | 117 | 72 | 84 | 95 | 145 | 161 |
| 11 | T415C | | | 146 | 143 | 125 | 105 | 86 | 112 |
| 12 | T415A | | | 115 | 164 | 132 | 107 | 79 | 105 |
| 13 | M622L | | | 117 | 41 | 59 | 85 | 90 | 142 |
| 14 | I621V | | | 113 | 39 | 70 | 71 | 48 | 48 |
| average | wild-type | | | 100 | 100 | 100 | 100 | 100 | 100 |
| st. dev. | | | | 7 | 10 | 5 | 3 | 6 | 13 |

Example 4: Activity Determination on ONPG as Substrate

The activity determination using o-nitrophenyl-β-D-galactopyranoside (ONPG) as the substrate was essentially according to the procedure described in the Food Chemical Codex (FCC 8$^{th}$ edition, p 1319-1320: Lactase (neutral) β-galactosidase activity).

The samples produced in Example 2 were diluted 200-fold until ~0.1 neutral lactase units (NLU) per mL using buffer A (100 mM potassium phosphate (pH6.5) containing 0.05 mM EDTA, 0.1 mM MgSO4 and 0.2% (W/V) TRITON™ X100). The same buffer, but without TRITON™ X100, is used for the preparation of the substrate (50 mg o-nitrophenyl-β-D-galactopyranoside (Sigma-Aldrich) in 20 mL). After preheating the substrate the following is mixed together: 125 μL of substrate and 25 μL of sample. The reaction is allowed to proceed for 10 minutes at 37° C., after which the reaction is stopped by the addition of 25 μL sodium carbonate (30 g/L) and 20 μL of ultrapure water. The resulting absorbance at 405 nm can be used and compared to the calibration curve made from o-nitrophenol (ONP).

The measurements occurred on a Konelab clinical analyzer (Thermo Scientific Arena 30). Calculation of the activity was performed as described in the Food Chemical Codex and corrected for the difference in assay temperature. The correction factor was 1.25 and was established empirically. The specific activity of the different lactase variants was determined by dividing these values by the protein dosage (as determined in Example 3) in the assay and the result is depicted in Table 3.

Example 5: Activity Determination on Lactose as Substrate

The samples were diluted to ~0.4 NLU/mL in buffer B (100 mM sodium phosphate (pH6.5) containing 0.05 mM EDTA and 1 mM MgSO4). The substrate consisted of 4.8% lactose monohydrate dissolved in buffer B. The enzyme mix consisted of 780 units of horseradish peroxidase (Sigma Aldrich), 0.25 units of glucose oxidase (DSM) and 12.5 mg (+/−1 mg) 2,2'-Azino-bis(3-ethylbenzothiazoline-6-sulfonic acid) diammonium salt (ABTS, Sigma Aldrich) in a total of 10 mL of buffer B. The assay is measured relatively against a serial dilution of neutral lactase (0.1-0.8 NLU/mL). For the reaction to occur the following is transferred to one well of a standard microtiter plate: 25 μL buffer B, 25 μL of sample or standard, 25 μL of enzyme mix. After pre-incubation for 10 minutes, 175 μL of substrate is added and the reaction is measured on a MTP reader (Tecan Infinity M1000) at 420 nm and 30° C. for 30 minutes. The absorbance is measured every 30 seconds and the slope per five data points (2.5 minutes) was calculated. The maximum slope over the complete assay is used to calculate the activity. This maximum slope is expressed as μmol glucose produced by lactase per min under the conditions described here (LACU). The specific activity of the different lactase variants is calculated by dividing these values by the protein concentration in mg/ml (as determined in Example 3) in the assay. The specific activity in LACU/mg of these lactase variants is depicted in Table 3. A high specific activity on lactose may lead to a lower dosage of the enzyme in possible applications.

Example 6: Activity Determination in the Presence of Galactose

The samples were diluted to ~0.4 NLU/mL in buffer B. The substrate consisted of 4.8% lactose monohydrate dissolved in buffer B. The enzyme mix consisted of 780 units of horse radish peroxidase (Sigma Aldrich), 0.25 units of glucose oxidase (DSM) and 12.5 mg (+/−1 mg) 2,2'-Azino-bis(3-ethylbenzothiazoline-6-sulfonic acid) diammonium salt (ABTS, Sigma Aldrich) in a total of 10 mL of buffer B. The inhibition buffer C consisted of 1500 mM galactose (purity >99.9%) in buffer B. The assay is measured relatively against a serial dilution of neutral lactase (0.1-0.8 NLU/mL). For the reaction to occur the following is transferred to one well of a standard microtiterplate: 25 μL buffer C (except for the standards), 25 μL of sample or standard, 25 μL of enzyme mix. After pre-incubating for 10 minutes, 175 μL of substrate is added and the reaction is measured on a MTP reader at 420 nm and 30° C. for 30 minutes. The absorbance is measured every 30 seconds and the slope per five data points was calculated. The maximum slope over the complete assay is used to calculate the activity. This maximum slope is expressed as μmol glucose produced by lactase per min under the conditions described here (LACGU). The specific activity in LACGU/mg of the different lactase variants is calculated by dividing these values by the protein concentration in mg/ml (as determined in Example 3) in the assay and the results are shown in Table 3.

The percentage inhibition by galactose is calculated using the formula

% inhibition=100*(x−y)/x where x stands for the specific activity in LACU/mg lactase as described in Example 5, and y stands for the specific activity in LACGU/mg lactase as described in Example 6. The results of the calculation of the % inhibition are shown in Table 3. A low % inhibition may lead to a higher activity at conditions in the application where lactose concentration is low and galactose concentration is high, when a low residual lactose concentration is required.

Example 7: Activity Determination in Milk at Low Temperature 1 mL of commercial semi-skimmed UHT milk (Campina) was mixed with 0.2 mL enzyme (~20 NLU/mL) as produced in Example 2, in deep well microtiter plates. The samples were incubated under static conditions for 4, 24 or 48 hours at 6° C. After this incubation the reactions were terminated by a heat treatment at 90° C. for 6 minutes, after which samples were directly placed in a freezer at −20° C. until analysis. Sample preparation for NMR was performed as follows: 48 μL 4.0 M HCl was added and the plates were sealed and mixed by tilting. Then, the plates were shaken for 20 minutes at 600 rpm and subsequently centrifuged for 10 minutes at 4750 rpm. From the clear supernatant 0.3 mL was transferred to a new plate and combined with 0.2 mL of a solution containing 20 g/L maleic acid (internal standard) and 40 g/L EDTA in $D_2O$. The plates were sealed, mixed by tilting and briefly centrifuged. After lyophilization, the residue was dissolved in 0.05 mL D20 and lyophilization was repeated. The dried residue was dissolved in 0.7 mL D20, again lyophillized overnight and again dissolved in 0.7 mL $D_2O$. After careful mixing, the samples were centrifuged for 10 minutes at 4750 rpm and 0.6 mL was transferred to a NMR tube. The samples were measured on a Bruker Avance III spectrometer equipped with a cryoprobe operating at a proton frequency of 700 MHz at a probe temperature of 290K. The samples were measured in single fold using 8 scans and a delay of 30 seconds. From the NMR spectra the following compounds were quantified: Lactose ($\delta$=4.67 (d)), glucose $\delta$=4.64 (d), galactose $\delta$=4.58 (d) and galacto oligo saccharide (GOS, integral of the area from $\delta$=4.52 to approx. $\delta$=4.38). In Table 3 the amount of glucose detected after 4 hours incubation per mg added enzyme is indicated. Also the amount of GOS after 48 hours, when most lactose is hydrolysed and little residual lactose is left (<0.5 g/l), is depicted.

A high lactose hydrolysis activity of the enzyme in milk at a low temperature (4-12° C.) may lead to a reduced dosage of the enzyme in such an application relevant for the dairy industry, and therefore reduced cost. An increased GOS production may lead to a prebiotic effect of the produced milk.

Example 8: Combinations of Lactase Variants

Different combinations of mutations in the lactase gene were generated as described in Example 1, except that multiple amino acid changes were combined in the expression product of a gene construct. The different variants containing these combined amino acid changes are depicted in Table 4. Position of the change is indicated in comparison with the wild type *K. lactis* beta-galactosidase amino acid sequence (SEQ ID NO: 2).

TABLE 4

Amino acid changes introduced in the protein sequence of *K. lactis* beta-galactosidase. Amino acids are depicted according to the single letter annotation

| Variant# | Mutations | | | | |
|---|---|---|---|---|---|
| 15 | Y440F | V619I | T633G | | |
| 16 | Y440F | V619I | A483S | | |
| 17 | Y440F | V619I | T633G | A258T | A483S |
| 18 | Y440F | V619I | T415A | A258T | A483S |
| 19 | Y440F | V619I | T633G | L862V | |
| 20 | Y440F | V619I | T415A | L862V | |
| 21 | Y440F | V619I | T415C | L862V | |
| 22 | Y440F | V619I | A483S | L862V | |
| 23 | Y440F | T415A | | | |
| 24 | T415A | A483S | | | |
| 25 | T415C | A483S | | | |
| 26 | T633G | A483S | | | |
| 27 | Y440F | V619I | T415C | | |

TABLE 4-continued

Amino acid changes introduced in the protein sequence of *K. lactis* beta-galactosidase. Amino acids are depicted according to the single letter annotation

| Variant# | Mutations | | | | |
|---|---|---|---|---|---|
| 28 | V619I | A483S | T415A | | |
| 29 | A258T | V619I | A483S | T415A | |
| 30 | A258T | V619I | T633G | T415A | A483S |
| 31 | A258T | V619I | Y440F | E264V | A483S |
| 32 | A258T | V619I | Y440F | L862V | E264V | A483S |
| 33 | L862V | V619I | T633G | T415A | |
| 34 | A483S | V619I | T415A | L862V | |
| 35 | A483S | V619I | T633G | L862V | |
| 36 | L862V | V619I | E264V | A483S | |

Again, the modified lactase genes were expressed in *E. coli* and lactase protein was isolated as described in Example 2. The amount of lactase protein that was expressed was determined as described in Example 3. The activity of these enzyme samples on the hydrolysis of lactose was determined as described in Example 5 and compared to the activity of the wild type enzyme expressed and isolated exactly the same way. Also the activity of the enzyme samples on the hydrolysis of lactose in milk at low temperature after 4 hours was determined as described in Example 7.

The specific activity of the different lactase variants is calculated by dividing the measured values by the lactase protein concentration in mg/ml in the assay. The specific activity of these lactase variants in both assays was expressed as relative activity compared to the activity of the wild type enzyme obtained in the same assays. For this the specific activity of the wild type lactase was set at 100 in both assays, and the calculated specific activities of the variants was related to this. The results of this analysis are depicted in Table 5.

TABLE 5

Results of the analysis of the (specific) activity of the variants in the various assays. Values are depicted as relative to the value found with wild type lactase that are significantly ($p < 0.05$) higher from the average of wild-type lactases are marked.

| Variant | Mutation | | | | | Relative specific activity on lactose Example 8 | Relative activity in milk Example 8 |
|---|---|---|---|---|---|---|---|
| 15 | Y440F | V619I | T633G | | | 47 | 139 |
| 16 | Y440F | V619I | A483S | | | 115 | 107 |
| 17 | Y440F | V619I | T633G | A258T | A483S | 144 | 162 |
| 18 | Y440F | V619I | T415A | A258T | A483S | 130 | 122 |
| 19 | Y440F | V619I | T633G | L862V | | 46 | 118 |
| 20 | Y440F | V619I | T415A | L862V | | 145 | 116 |
| 21 | Y440F | V619I | T415C | L862V | | 135 | 114 |
| 22 | Y440F | V619I | A483S | L862V | | 119 | 134 |
| 23 | Y440F | T415A | | | | 138 | 74 |
| 24 | I415A | A483S | | | | 167 | 33 |
| 25 | I415C | A483S | | | | 142 | 61 |
| 26 | T633G | A483S | | | | 133 | 65 |
| 27 | Y440F | V619I | T415C | | | 144 | 106 |
| 28 | V619T | A483S | T415A | | | 154 | 61 |
| 29 | A258T | V619I | A483S | T415A | | 149 | 41 |
| 30 | A258T | V619I | T633G | T415A | A483S | 141 | 98 |
| 31 | A258T | V619I | Y440F | E264V | A483S | 135 | 100 |
| 32 | A258T | V619I | Y440F | L862V | E264V A483S | 128 | 96 |
| 33 | L862V | V619I | T633G | T415A | | 122 | 106 |
| 34 | A483S | V619I | T415A | L862V | | 153 | 102 |
| 35 | A483S | V619I | T633G | L862V | | 169 | 99 |
| 36 | L862V | V619I | E264V | A483S | | 118 | 78 |
| average wild-type | | | | | | 100 | 100 |
| st. dev. | | | | | | 6 | 6 |

From this analysis it can be deduced that several combination variants show advantageous lactose hydrolysis in both assays.

The invention claimed is:

1. A variant polypeptide having at least 90% sequence identity with SEQ ID NO: 2, and having lactase activity, wherein the variant polypeptide:
comprises at least one substitution of an amino acid residue corresponding to any of amino acids 233, 257, 258, 263, 274, 284, 297, 415, 440, 483, 619, 621, 622, 633, 862 or 1004 set forth in SEQ ID NO: 2; wherein the at least one substitution produces one or more altered properties selected from the group consisting of increased specific activity on o-nitrophenyl-β-D-galactopyranoside (ONPG), increased specific activity on lactose, increased activity on lactose in milk at 4° C. to 12° C., reduction in galactose inhibition, and increased galacto-oligosaccharide (GOS) production in milk, as compared with the polypeptide of SEQ ID NO: 2.

2. The variant polypeptide of claim 1, wherein the one or more altered property is increased specific activity on o-nitrophenyl-β-D-galactopyranoside (ONPG) as compared with the polypeptide of SEQ ID NO:2.

3. The variant polypeptide of claim 2, wherein the variant polypeptide comprises at least one substitution of an amino acid residue corresponding to any of the amino acids 415, 483, 619, 621, 622 or 633.

4. The variant polypeptide of claim 2, wherein the variant polypeptide comprises at least one substitution selected from T415C, T415A, A483S, V619I, I621V, M622L or T633G.

5. The variant polypeptide of claim 1, wherein the one or more altered property is increased specific activity on lactose as compared with the polypeptide of SEQ ID NO:2.

6. The variant polypeptide of claim 5, wherein the variant polypeptide comprises at least one substitution of an amino acid residue corresponding to any of the amino acids 415, 440 or 483.

7. The variant polypeptide of claim 5, wherein the variant polypeptide comprises at least one substitution selected from T415C, T415A, Y440F or A483S.

8. The variant polypeptide of claim 1, wherein the one or more altered property is increased activity on lactose in milk as compared with the polypeptide of SEQ ID NO:2.

9. The variant polypeptide of claim 8, wherein the variant polypeptide comprises at least one substitution of an amino acid residue corresponding to any of the amino acids 233, 257, 258, 263, 274, 284, 297, 440, 619, 633, 862 or 1004.

10. The variant polypeptide of claim 8, wherein the variant polypeptide comprises at least one substitution selected from D233V, D257G, A258T, N263S, K274E, N284S, E297G, Y440F, V619I, T633G, L862V or A1004P.

11. The variant polypeptide of claim 8, wherein the variant polypeptide comprises at least two substitutions selected from N263S, K274E or N284S.

12. The variant polypeptide of claim 8, wherein the variant polypeptide comprises at least substitutions D257G and E297G.

13. The variant polypeptide of claim 1, wherein the one or more altered property is decreased galactose inhibition as compared with the polypeptide of SEQ ID NO:2.

14. The variant polypeptide of claim 13, wherein the variant polypeptide comprises at least one substitution of an amino acid residue corresponding to any of the amino acids 619, 621 or 622.

15. The variant polypeptide of claim 13, wherein the variant polypeptide comprises at least one substitution selected from V619I, I621V or M622L.

16. The variant polypeptide of claim 1, wherein the one or more altered property is increased galacto-oligosaccharide (GOS) production in milk as compared with the polypeptide of SEQ ID NO:2.

17. The variant polypeptide of claim 16, wherein the variant polypeptide comprises at least one substitution of an amino acid residue corresponding to any of the amino acids 619 or 622.

18. The variant polypeptide of claim 16, wherein the variant polypeptide comprises at least one substitution selected from V619I or M622L.

19. A composition comprising the variant polypeptide according to claim 1, and at least one component selected from salt, preservative, polyol or metal ions.

20. The variant polypeptide of claim 1, wherein the variant polypeptide is used in preparation of a low lactose or lactose free dairy product.

21. The variant polypeptide of claim 1, wherein the variant polypeptide has at least 95% sequence identity with SEQ ID NO:2.

22. The variant polypeptide of claim 1, wherein the variant polypeptide has at least 96% sequence identity with SEQ ID NO:2.

23. The variant polypeptide of claim 1, wherein the variant polypeptide has at least 97% sequence identity with SEQ ID NO:2.

24. The variant polypeptide of claim 1, wherein the variant polypeptide has at least 98% sequence identity with SEQ ID NO:2.

25. The variant polypeptide of claim 1, wherein the variant polypeptide has at least 99% sequence identity with SEQ ID NO:2.

* * * * *